(12) United States Patent
Villa et al.

(10) Patent No.: US 7,530,965 B2
(45) Date of Patent: May 12, 2009

(54) PROTECTIVE DEVICE FOR A NEEDLE

(75) Inventors: Danilo Villa, Viadana (IT); Emanuele Minari, Brescello (IT)

(73) Assignee: Delta Med S.R.L., Viadana (IT)

( * ) Notice: Subject to any disclaimer, the term of this patent is extended or adjusted under 35 U.S.C. 154(b) by 795 days.

(21) Appl. No.: 10/485,242

(22) PCT Filed: Jul. 30, 2002

(86) PCT No.: PCT/EP02/08534

§ 371 (c)(1),
(2), (4) Date: Jun. 28, 2004

(87) PCT Pub. No.: WO03/011381

PCT Pub. Date: Feb. 13, 2003

(65) Prior Publication Data

US 2004/0225260 A1    Nov. 11, 2004

(30) Foreign Application Priority Data

Jul. 31, 2001    (IT)    ............................. BO2001A0497

(51) Int. Cl.
*A61M 5/00*    (2006.01)
(52) U.S. Cl. ..................................... 604/110
(58) Field of Classification Search ................... 604/19, 604/48, 93.01, 110, 164.01, 164.07–164.08, 604/167.06, 263–264; 128/919
See application file for complete search history.

(56) References Cited

U.S. PATENT DOCUMENTS

| | | | |
|---|---|---|---|
| 4,834,718 A * | 5/1989 | McDonald | 604/195 |
| 5,051,109 A | 9/1991 | Simon | |
| 5,205,829 A * | 4/1993 | Lituchy | 604/164.08 |
| 5,279,591 A * | 1/1994 | Simon | 604/263 |
| 5,300,045 A | 4/1994 | Plassche, Jr. | |
| 5,344,408 A | 9/1994 | Partika | |

(Continued)

FOREIGN PATENT DOCUMENTS

DE    201 03 363 U1    6/2001

(Continued)

OTHER PUBLICATIONS

PCT International Preliminary Examination Report, (PCT Article 36 and Rule 70), International Application No. PCT/EP02/08534, 6 pages, Nov. 10, 2003.

(Continued)

*Primary Examiner*—Nicholas D Lucchesi
*Assistant Examiner*—Aarti Bhatia
(74) *Attorney, Agent, or Firm*—Steven J. Rosen

(57) ABSTRACT

Protective device for a needle, more particularly for a catheter introducing needle or so-called cannula needle, whereby this protective device comprises protective means which slidably cooperate with the needle, characterized in that said protective means comprise a combination of at least, on one hand, safety means having at least one part which, upon retraction of the needle through the protective means, is placed in front of the needle point and prevents the re-use of the needle, and, on the other hand, blocking means which cooperate with the safety means and which, when the protective device passes from a non-operative state into an operative state, release said safety means from a blocked position into an unblocked position.

19 Claims, 5 Drawing Sheets

U.S. PATENT DOCUMENTS

| | | | | |
|---|---|---|---|---|
| 5,419,766 A | * | 5/1995 | Chang et al. | 604/110 |
| 5,531,701 A | * | 7/1996 | Luther | 604/165.04 |
| 5,533,988 A | * | 7/1996 | Dickerson et al. | 604/523 |
| 5,599,310 A | * | 2/1997 | Bogert | 604/164.12 |
| 5,800,395 A | * | 9/1998 | Botich et al. | 604/110 |
| 5,846,227 A | * | 12/1998 | Osterlind | 604/164.08 |
| 5,853,393 A | * | 12/1998 | Bogert | 604/165.02 |
| 5,910,132 A | * | 6/1999 | Schultz | 604/162 |
| 5,911,705 A | * | 6/1999 | Howell | 604/110 |
| 5,957,893 A | * | 9/1999 | Luther et al. | 604/164.01 |
| 6,117,108 A | * | 9/2000 | Woehr et al. | 604/110 |
| 6,203,527 B1 | * | 3/2001 | Zadini et al. | 604/110 |
| 6,254,574 B1 | * | 7/2001 | Burzynski et al. | 604/170.01 |
| 6,709,419 B2 | * | 3/2004 | Woehr | 604/164.07 |
| 6,972,002 B2 | * | 12/2005 | Thorne | 604/164.08 |
| 6,984,213 B2 | * | 1/2006 | Horner et al. | 600/564 |
| 7,004,927 B2 | * | 2/2006 | Ferguson et al. | 604/110 |
| 7,008,402 B2 | * | 3/2006 | Ferguson et al. | 604/110 |
| 7,357,784 B2 | * | 4/2008 | Ferguson | 604/110 |

FOREIGN PATENT DOCUMENTS

WO     WO 99/08742     2/1999

OTHER PUBLICATIONS

International Search Report, International Application No. PCT/EP 02/08534, 3 pages, Feb. 13, 2003.

* cited by examiner

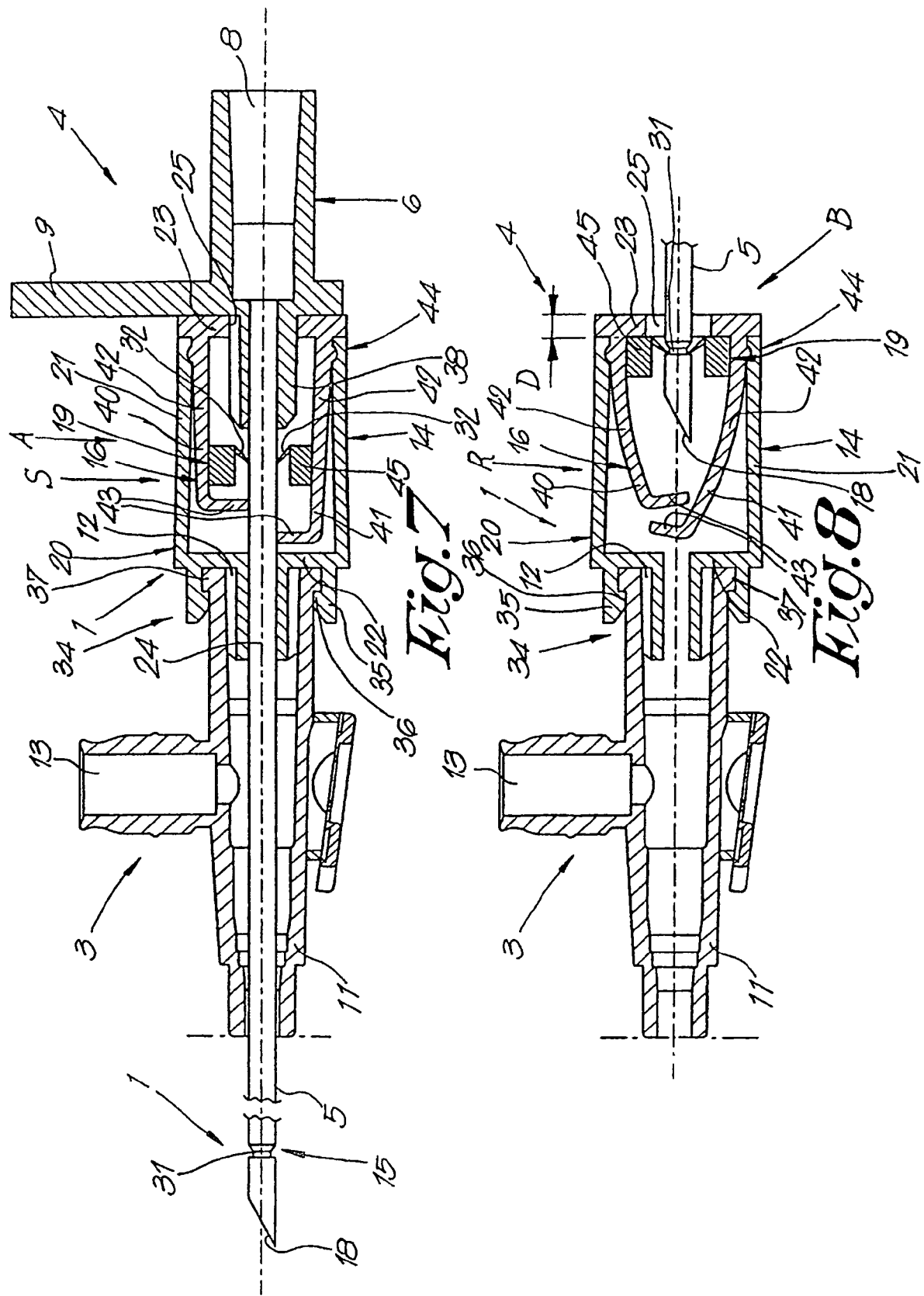

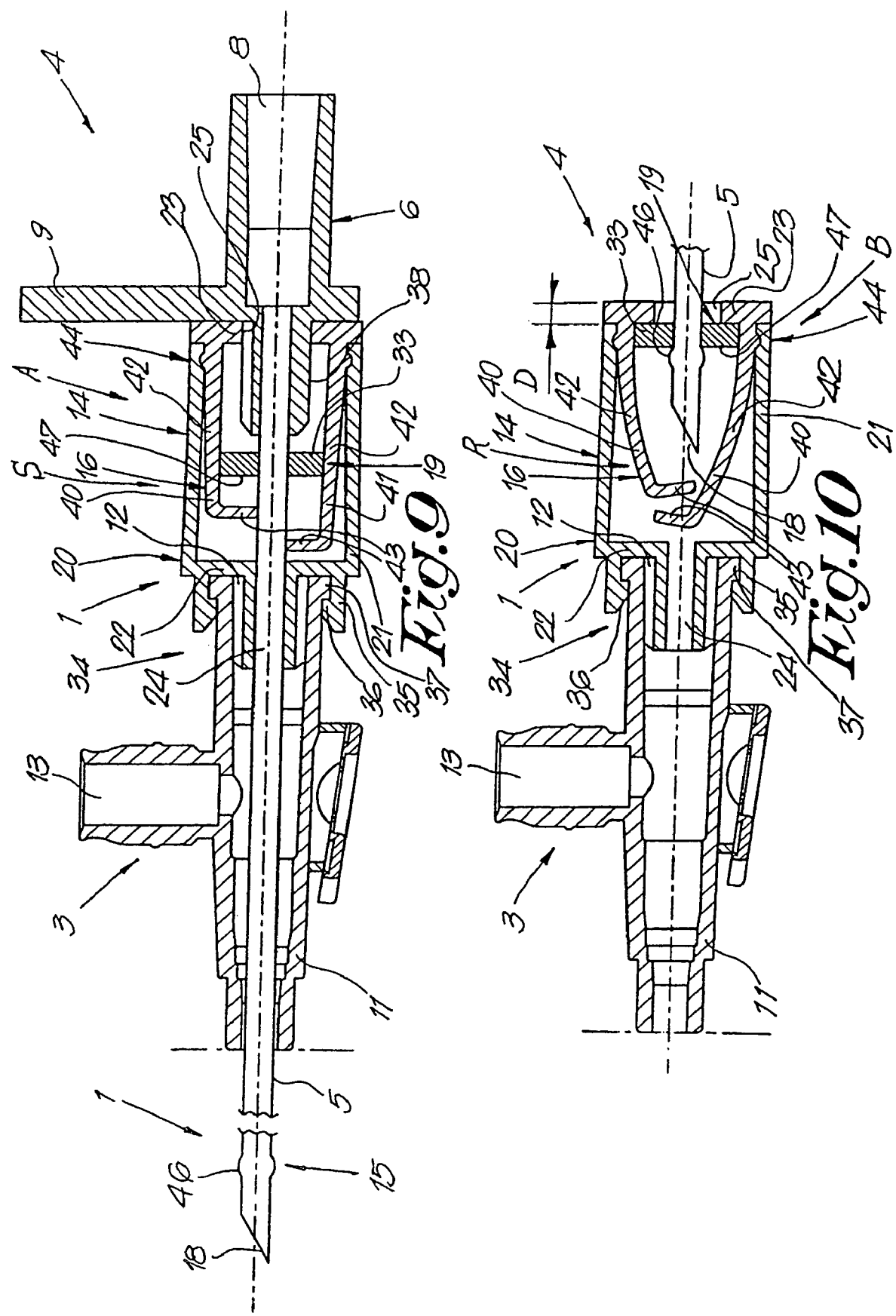

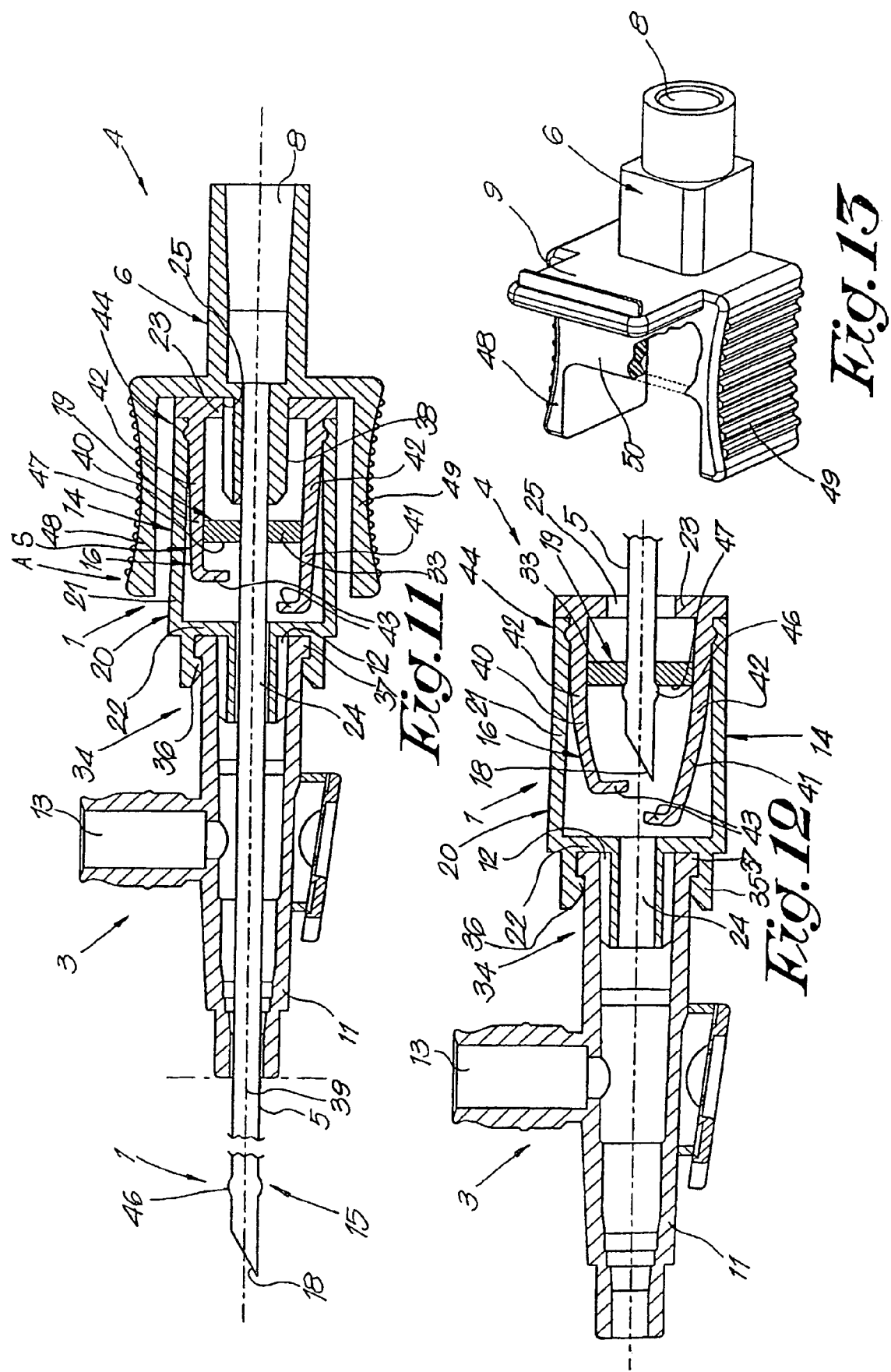

PROTECTIVE DEVICE FOR A NEEDLE

BACKGROUND OF THE INVENTION

This invention is situated within the technical field of medical and surgical products and relates to a protective device for a needle.

In first instance, the invention is intended to be used in combination with a catheter introducing needle or cannula needle, however, in general it is not excluded to use it in combination with other types of surgical needles.

More particularly, the invention relates to a protective device which is capable of avoiding accidental pricking or wounds being inflicted on health staff during the use of the needles concerned.

In case of a cannula needle assembly the operator is inserting the cannula and the needle which is provided in this cannula, by perforating the skin near the patient's vein or artery and introducing the needle and cannula with their tip into said vein or artery. Once the needle is inserted, the cannula remains in position, partially within the vein, while the needle, which has fulfilled its function, is taken out by the operator.

This is the phase during which the sharp point of the extracted needle is dangerously exposed, with a high risk of pricking or wounding the operator.

The operation involving replacing the needle into a protective hood is equally dangerous for the operator replacing it, as numerous specialised studies have shown statistically.

In order to avoid this problem and to guarantee the safety of health staff during their activity, various kinds of protection devices applicable to cannula needles have been developped.

Safety cannula needle assemblies are known, having a protective device allowing that the needle can be retracted within a protective element, which may be part of the assembly itself, whereby the withdrawal is obtained by activating a lever which pushes the needle correspondingly into the protective element, or manually, by manipulating an external handle connected to the needle which can slide along the axis of the protective element, thereby permitting withdrawal of the needle itself.

The main disadvantage of these devices, which are already known to the profession, is the considerable volume of the protective element which may make it laborious and difficult for the operator to use these cannula needles, resulting in that this known system is less practical and versatile.

Another disadvantage of these protective devices, which are already known to the profession, is not only that they are complicated or composed of a large number of parts, but also that they entail risks of not working properly and that high production costs are involved in producing each of the composing parts and in assembling them.

A further disadvantage is that extra operations are necessary compared to unprotected devices, entailing the risk of omissions or wrongly executed operations by the operator.

The profession is also acquainted with protective devices for cannula needles involving the use of a pair of rings linked by a flexible wire. The first ring is fixed to the base of the needle, while the second is fixed to the end of the cannula and is intended to guide extraction of the needle and to contain its point. The mechanism makes the needle slide, during its extraction, through the axial forum of the second ring until its further extraction is stopped by the fixed length of flexible wire. Hereby, the needle arrives with its needle point into one of the rings. The needle, fitted into the ring with its point protected, can be safely pulled out of the cannula with the entire device comprising the two rings and the wire.

The main disadvantage of this device is the considerable encumbrance entailed by the two protective rings and above all by the flexible wire, which can make it laborious and difficult to use the cannula needle, reducing its functional scope.

A further disadvantage of these rings and in general of all the devices known to the profession, is that the patient's body fluids, and sometimes drugs, which may be deposited on the needle as drops or as an adhesive covering, are still accessible and/or that there still is a considerable risk that these fluids or drugs leave the protective device. Shocks may cause them to squirt on the bare skin or into the eyes of the operators or of others standing in the proximity thereof, entailing the risk of infection or contamination.

The main object of this invention is to provide a protective device for needles, more particularly for cannula needles, which allows to considerably reduce the risk of contact with patient's body fluids or with drugs on the needle, and which prevents that an accidental pricking and the causing of wounds may happen, all this by means of a device which is compact, resulting in that it is also easy to use and in that it is very versatile.

A further aim is to provide a protective device that is easy to construct and assemble and hence not expensive.

Furthermore, this protective device ensures maximum protection for the operator during extraction of the needle from the cannula.

BRIEF DESCRIPTION OF THE INVENTION

To this end, the invention relates to a protective device for a needle, more particularly for a catheter introducing needle or so-called cannula needle, whereby this protective device comprises protective means which slidably cooperate with the needle, which device is characterized in that said protective means comprise a combination of at least, on one hand, safety means having at least one part which, upon retraction of the needle through the protective means, is placed in front of the needle point and prevents the re-use of the needle, and, on the other hand, blocking means which cooperate with the safety means and which, when the protective device passes from a non-operative state into an operative state, release said safety means from a blocked position into an unblocked position.

The fact that, according to the invention, a combination is made of safety means with blocking means, which automatically release the safety means from a blocked into an unblocked position, offers the advantage that the device functions very efficiently, as will be clear from the following detailed description.

According to a preferred embodiment, the safety means and the blocking means are configured in such a manner that, upon retraction of the needle, the safety means, more particularly the part or parts which are placed in front of the needle point, remain at a distance from the needle during the entire retraction thereof. In other words, during the complete retraction, there is no contact between, on the one hand, the safety means, more particularly said safety tongue or safety tongues, and, on the other hand, the needle. As a result thereof, the safety means, more particularly said tongues, will never urge fluids adhered to the needle towards the needle point and off the needle point. In this manner, it is avoided that fluids are scraped completely from the needle and can consequently leave the protective device.

In the most preferred embodiment, said blocking means are shiftable in respect to the safety means, such that, by means of a shifting movement of the blocking means, the safety means are released from a blocked position into an unblocked position, whereby said blocking means cooperate with the needle in such a manner that a displacement and retraction of the needle also causes the above shifting movement of the blocking means. In this way, with a minimum of constructive parts, a device is offered which can be actuated automatically, just by the retraction of the needle.

In a practical embodiment, the blocking means substantially consist of a sliding ring located around the needle.

Preferably, the abovesaid part or parts are elastically bendable and consist of safety tongues, such that these parts are automatically urged into the path of the needle upon retraction of the latter. In such case, the blocking means can be formed of an element, such as a ring, which in the non-operative state of the protective device, keeps said parts out of the path of the needle.

Further, the device is preferably characterized in that the protective means and the needle comprise stopping means, acting as abutment means between the protective means and the needle, which define an end position when retracting the needle, such that the needle cannot leave the protective means.

According to a further important preferred feature, the protective device is provided with scraping means to dry the needle when the device itself passes from the non-operative state to the operative state. These scraping means, which preferably consist of an O-ring, considerably improve the safety of the device, as will become clear from the further description.

Further, it is preferred that said protective means are provided with a rear wall having a rear side, whereby the scraping means in their outermost position remain located at a distance from the rear side of said rear wall. In respect to this, it should be noted that fluids, which are scraped or wiped from the needle, are collected in front of the scraping means. At the end, it is never excluded that these fluids may penetrate in between the scraping means and the needle surface by means of a pumping effect which may be created when moving the needle sidewards in respect to the scraping means. Due to this pumping effect, some fluid may arrive at the rear side of the scraping means. By preserving a distance between this rear side and the rear side of the rear wall, it is impossible that the operator which handles the device can come into contact with the fluid in question.

It is clear that the fact that the safety tongues do not come into contact with the needle during the entire retraction of the needle, is also advantageous in other protective devices for needles. Therefore, according to a second aspect, the invention also relates to a protective device for a needle, more particularly for a catheter introducing needle, whereby this protective device comprises protective means which slidably cooperate with the needle, characterized in that said protective means comprise one or more safety tongues which upon retraction of the needle are automatically positioned in front of the needle point, thereby preventing the needle from being re-used, whereby these tongues upon the complete retraction movement of the needle remain at a distance from the needle.

Also the abovesaid feature that scraping means, more particularly a scraping ring is used which for all conditions remain at a distance from the rear side or the rear wall of the protective device can be used in combination with other types of protective devices, which must not necessarily be equipped with blocking means. Therefore, according to a third aspect, the invention also relates to a protective device for a needle, more particularly for a catheter introducing needle, whereby this protective device comprises a housing which slidably cooperates with the needle such that the needle can be retracted upto a position in which the needle point is located in said housing, characterized in that said protective device comprises a scraping ring which cooperates with the needle, whereby this scraping ring is located inside the housing, at a distance from the rear side of the rear wall of said housing.

It is clear that the invention also relates to needles and safety cannula needle assemblies which are provided with a protective device of the invention.

Other features will become clear from the following detailed description and the appended claims.

BRIEF DESCRIPTION OF THE DRAWINGS

In order to better explain the features of the present invention, hereafter, several preferred embodiments are described as examples without being limitative, with reference to the accompanying drawings, in which:

FIG. 4 represents a cross-section lateral view similar as in FIG. 1, however, with the needle in retracted position and with the protective device being operative;

FIG. 6 represents a cross-section lateral view similar as in FIG. 4, however, after that the needle, together with the protective device, is separated from the cannula;

FIGS. 7 and 8 represent an alternative embodiment of the invention, for the non-operative and operative state respectively of the protection device;

FIGS. 9 and 10 represent a further alternative embodiment of the invention, for the non-operative and operative state respectively of the protection device;

FIGS. 11 and 12 represent a still further alternative embodiment of the invention, for the non-operative state and the state during retraction of the needle, respectively;

FIG.13 represents a perspective view of the part which in FIG. 11 is indicated by F13.

DETAILED DESCRIPTION OF THE INVENTION

Figure 1:
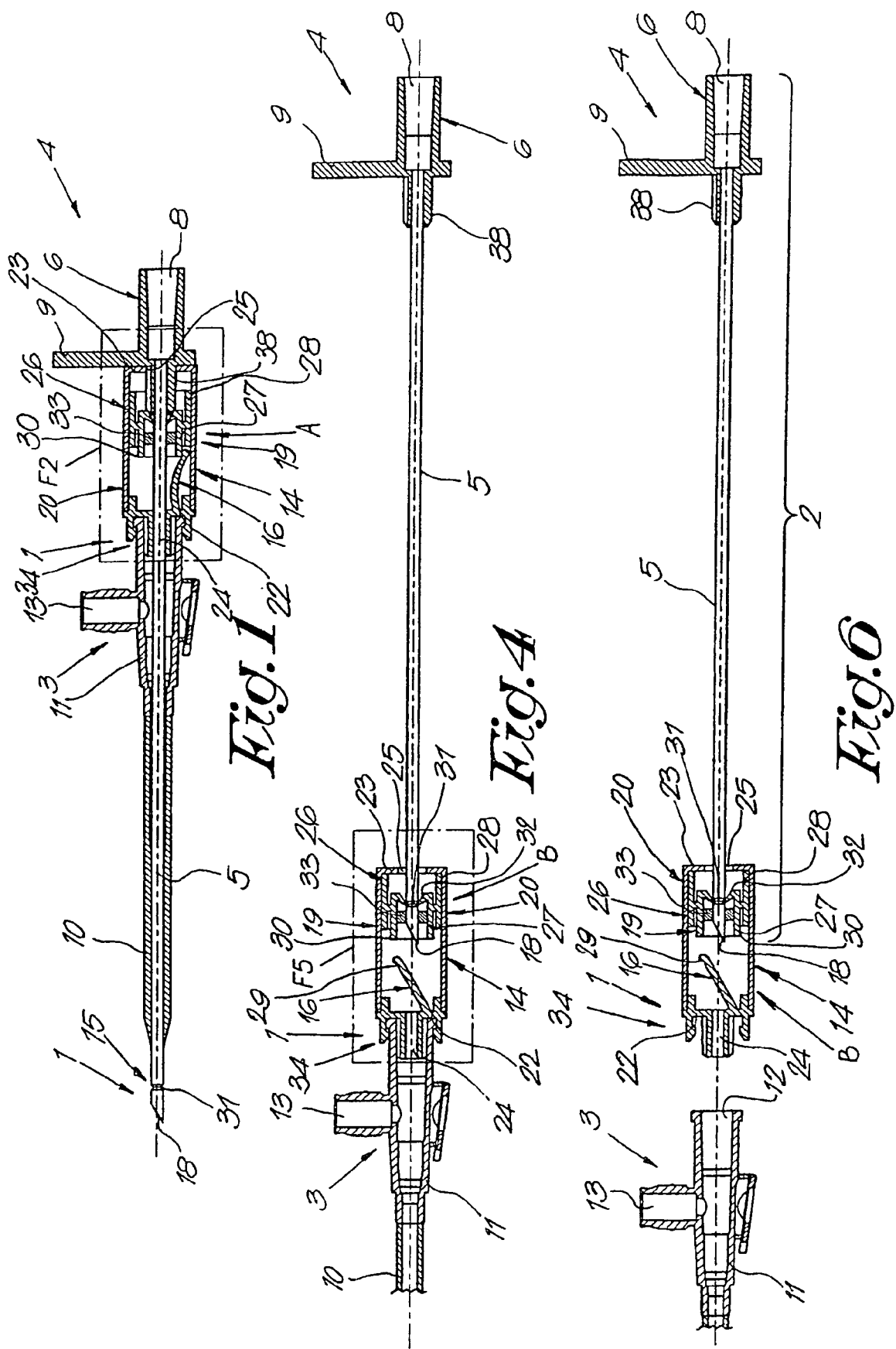
FIG. 1 represents a cross-section lateral view of a cannula needle assembly provided with a protective device according to the invention, said protective device being in non-operative state.

With reference to FIGS. 1 to 6, reference 1 in general indicates a protective device for a cannula needle 2, which cannula needle 2, together with the cannula 3, forms a complete cannula needle assembly 4.

With the cannula needle 2, the complete part is meant which is formed by the actual needle 5 and a needle hub 6 in which this needle 5 is attached. The needle 5 fits to the cannula 3 and is preferably hollow. The inner channel 7 is in connection with an opening 8 in the needle hub 6, which, for example allows a connection with a so-called flash chamber, or with any other accessory. As represented, the needle hub 6 may be provided with a support 9.

The cannula 3 is carried out in a conventional manner and mainly consists of an elongated hollow front portion 10, which is intended to be partly introduced in a vein of the patient and which furthermore comprises a rear portion 11 acting as a cannula hub which is provided with an entrance opening 12 for introducing the needle 5 into the cannula 3. The entrance opening 12 is also intended to be coupled to a tube for fluid supply or the like after retraction of the needle 5. As shown, the cannula 3 may be provided with one or more additional entrance openings 13. Of course, the cannula 3 may also be used for introducing other medical or surgical substances or elements, for example, for introducing a catheter by means of a vein, artery or the like into a patient's body.

The protective device 1 substantially consists of, on the one hand, protective means, generally indicated by reference 14, which slidably fit onto the needle 5, and, on the other hand, stopping means 15, acting as abutment means between the protective means 14 and the needle 5, which abutment means define an end position when retracting the needle 5 through the protective means 14.

Said protective means 14 comprise, on the one hand, safety means 16 having at least one part, in this case, a safety tongue 17, which, upon retraction of the needle 5, is placed in front of the point 18 of the needle 5, such as to prevent the re-use of this needle and, on the other hand, blocking means 19 which cooperate with the safety means 16 and which, when the protective device passes from a non-operative state A into an operative state B, release said safety means 16 from a blocked position into an unblocked position, as described in detail in the following.

As shown, the safety means 16 and the blocking means 19 are preferably incorporated in a hollow body or housing 20 having a side wall 21 and two opposed end walls 22-23, which are each provided with a passage opening 24-25 for the needle 5.

Figure 5:
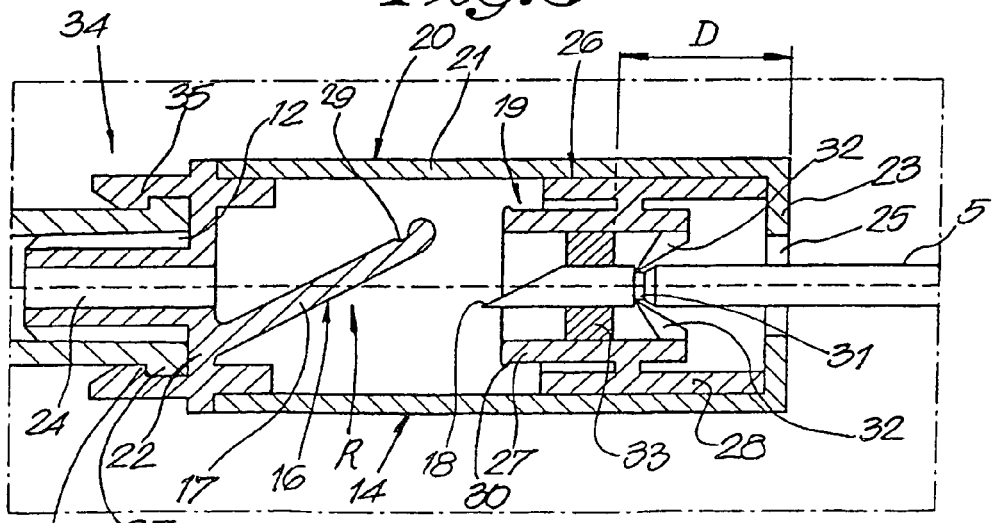
FIG. 5 represents an enlargement of the portion which is indicated by F5 in FIG. 4.

The safety tongue 17 consists of an elastically bendable lip, which in this case forms one part with the end wall 22, and which is configured and arranged in such a manner that, in its free position, it extends through the path of the needle 5, preferably in an oblique manner, as shown in FIGS. 4 to 6.

The blocking means 19 comprise an element which is shiftably fitted in the hollow body 20, which element, in the represented example, consists of a ring 26 composed of an inner cylindrical ring part 27 and an outer cylindrical ring part 28 fixedly connected to each other. The outer cylindrical ring part precisely fits into the hollow body 20.

Figure 2:
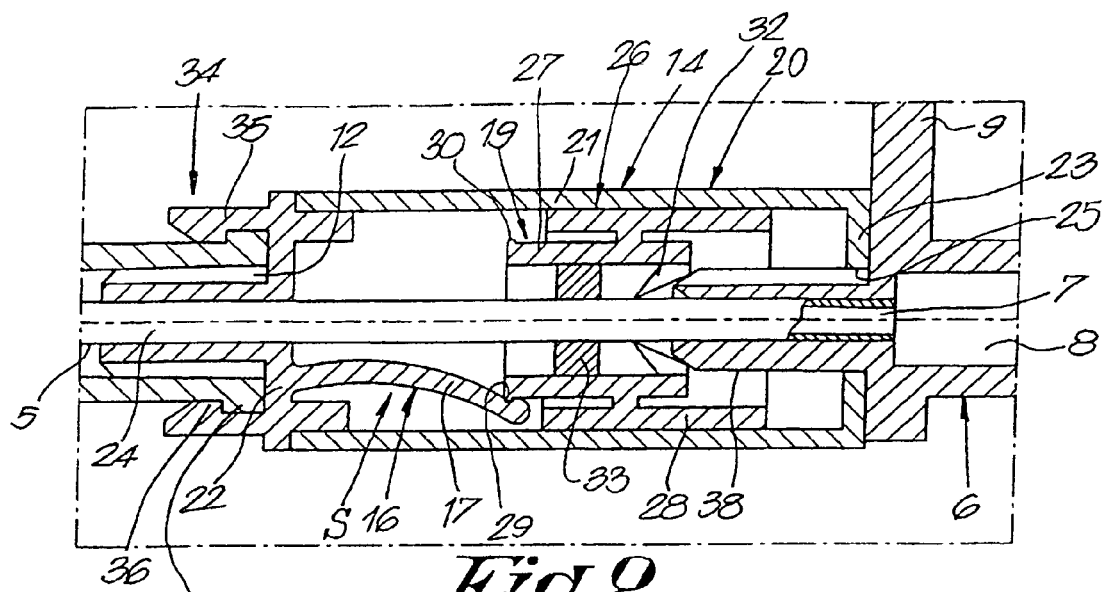
FIG. 2 represents an enlargement of the portion which is indicated by F2 in FIG. 1.
Figure 3:
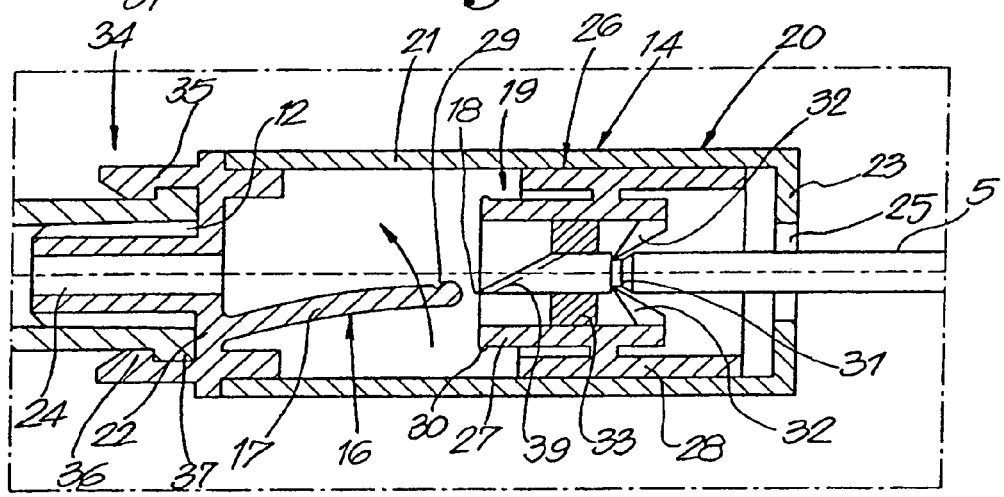
FIG. 3 represents the portion shown in FIG. 2, during retraction of the needle.

The ring 26 is configured such that, in the non-operative state A of the protection device 1, in which the needle 5 is completely inserted into the cannula 3, the ring 26 cooperates with the safety tongue 17 such that the latter is bent outwardly, in an open position S, in which this tongue 17 is not interfering with the needle 5. Hereby, as shown in FIGS. 1 and 2, the tongue 17 and the ring 26, more particularly the outer ring part 28, are slightly hooking behind each other, by means of a recess 29 in the free end of the tongue 17 and a collar 30 at the front outer end of said ring part 28.

The above mentioned stopping means 15 consist of abutment parts which are provided at the needle 5 and at the protective means 14, respectively. In the embodiment of FIGS. 1 to 6, these abutment parts are formed by an annular groove 31 nearby the point of the needle 5 and retaining means consisting of strips or fins 32 directed towards the axis of the ring 26 and inclined in the direction opposite to the extraction direction of the needle 5.

Furthermore, the protective device 1 is provided with scraping means 33 to dry the needle 5 sliding through it, thereby freeing it from blood or other body fluids from the patient. These scraping means 33 consist of a ring, membrane or disk having a central opening, or the like, fitting with a certain tension around the needle 5, which ring, membrane or disk preferably is made of a flexible synthetic material. More particularly, these means are formed by an O-ring.

The protective means 14, more particularly the housing 20, is carried out as an extension piece, which can be coupled to the catheter hub. To this end, the housing is provided with coupling means 34 at the end wall 22, allowing a releasable connection with said catheter hub, preferably by means of a snap connection. To this end, in the represented embodiment, said coupling means 34 comprise a number of elastically bendable fins 35, having locking portions 36 which can cooperate with a collar 37 at the rear edge of the rear portion of the cannula 3.

As shown, the needle hub preferably comprises at least one part 38 which, in the most forward position of the needle 5, cooperates with the protective means 14, thereby preventing the blocking means 14 from carrying out a shifting movement from the non-operative position A to the operative position B. This is obtained in that this part 38 extends through the opening 25 into the hollow body 20, thereby forming an obstacle for the displacement of the blocking means 14. More particularly, as shown in FIG. 2, said shifting is prevented in that the free end of part 38 comes into contact with said inner ring part 27 and/or said fins 35.

The functioning of the protective device 1 is substantially as described in the following.

Once the needle 5 and the cannula 3 are inserted into a patient's vein or artery, the needle 5 is retracted from the cannula 3, resulting in that the protective means 14 are automatically activated and are put from a non-operative state A into an operative state B.

In the beginning, in the non-operative state A, the part 38 is in contact with the inner ring part 27, resulting in that the blocking means 14 are prevented from being displaced, resulting in that the safety tongue 17 is kept in the position, as shown in FIGS. 1 and 2.

When retracting the needle 5, first, this needle freely slides through the protective means 14. From the moment on that the annular groove 31 arrives at the height of the fins 32, these fins are elastically urged into the annular groove 31, resulting in that the needle 5 cannot make any further sliding movement through the ring 26. As a consequence, the ring 26 is taken along with the movement of the needle 5, causing that the ring 26, in other words the blocking means 19, are freeing the tongue 17, which interposes itself between the passage opening 24 and the point 18 of the needle 5, corresponding to a state of release R.

Upon further retraction, the ring 26 will contact the end wall 23, as shown in FIG. 5, and, as a consequence thereof, any further extraction movement of the needle 5 from the protective means 14 is prevented. Hereafter, the cannula needle 2 can be disconnected from the cannula 3 by means of the releasable coupling means 34.

In this way, in the operative state B, the point 18 of the needle 5 cannot come out of the protective means 14 because it is blocked, in the direction of the opening 25 by the activation of the stopping means 15, and in the opposite direction by the tongue 17 which is interposed between the needle point 18 and the opening 24.

The protective means 14 are preferably configured in such a manner that any contact between the safety tongue 17 and the needle 5 is excluded for the complete retraction of the needle 5. In this way, it is excluded that the safety tongue 17 acts as a scraping element for the needle 5 and that, on the moment that the tongue 17 is released, blood or other fluids are projected through the passage opening 24 and possibly are contaminating this opening. In normal use, in the design of FIGS. 1 to 6 there will be no contact between the tongue 17 and the needle point 18 on the moment that the tongue 17 bends back into its free position. However, in order to exclude any contact, the point 18 can be further shortened, as indicated in dashed line 39 in FIG. 3.

The geometrical form and the inclination of the fins 32 make it possible to transfer the needle 5 towards the cannula 3 during the phase of assembly of the cannula needle assembly 4. Also the blocking means 19 are advantageous during the assembly, as by means of these blocking means 19, the tongue 17 can be kept in an non-activated state, allowing the free passage of the needle 5 to the protective means 14.

During the passage from the non-operative state A to the operative state B, the needle 5 slides through the scraping means 33 which dry it from the liquids that are adhered to this needle 5, thereby retaining these liquids in the hollow body 20. Hence, although the shaft of the needle 5 is no longer sterile, a decisive reduction of any infective or toxic products adhered at the needle 5 takes place, thereby reducing the risk for anyone who might have to touch the shaft of the needle 5 with bare hands. Furthermore, although the hollow body 20 is not completely closed, the fluids retained in it by the scraping means 33 are practically completely held inside, even if the needle 5 were to undergo shocks or vibrations.

In the embodiment of FIGS. 1 to 6, the coupling means 34 and the end wall 22 are made in one piece and together form a separate part which acts as a cover which is connected to the side wall 21 in any manner.

According to a variant, the coupling means 34 may also be moulded in a single piece with the hollow body 20.

FIGS. 7 and 8 show a second embodiment of the protective device 1 in which the safety means 16 consist of a pair of opposed elastically bendable safety tongues 40-41, facing each other and fixed to the end wall 23. The tongues 40-41 have a different length and consist of an elastically bendable first portion 42 which substantially extends in lengthwise direction and, at the distal end of this first portion 42, a second portion 43 which is directed transversely or substantially transversely in respect to the first portion 42. The safety tongues 40-41 are configured such that by means of their elasticity, they are permanently urged towards a position in which the second portions 43 are located in the path followed by the needle 5.

The end wall 23 is carried out in the form of a flange. This flange, together with the tongues 40-41 form an insertion piece, which, by means of a snap coupling 44, is mounted into the hollow body 20.

In this embodiment, the blocking means 19 consist of a ring 45 which is located around the needle 5 and in between the tongues 40-41, such that these tongues 40-41 by means of said ring 45 can be kept in an open state S, as shown in FIG. 7.

Similarly as in FIGS. 1 to 6, the ring 45 is provided with fins 32.

It should be noted that in FIG. 7 the configuration is chosen such that the tongues 40-41 are in contact with the ring 45, as well as in contact with the needle 5. Hereby, the tongues 40-41 are only in slight contact with the needle 5, resulting in that, during the retraction of the needle 5, no important frictional forces have to be surmounted.

It is clear that, according to alternative embodiments and dependent on the diameter of the ring 45 and/or the lengths of the second portions 43, there may or may not be a contact between the free ends of the tongues 40-41 and the needle 5.

In fact, the first aim of the blocking means 19 is to keep the tongues 40-41 separated from each other when no needle 5 is inserted in between, thereby allowing that, upon insertion of the needle 5 to the protective means 14, this needle 5 can be shifted through the hollow body 20.

During the passage from the non-operative state A to the operative state B, the fins 32 engage in the annular groove 31 of the needle 5 during the latter's axial sliding, thereby causing the ring 45 to slide towards the end wall 23. This sliding motion of the ring 45 permits the disengaging of the free ends of the tongues 40-41, so as to reach the state of release R, in which these free ends are curved towards each other, thus placing the tongues 40-41 between the passage opening 24 and the needle point 18. The different lengths of the tongues 40-41 allow the respective free ends to overlap each other, preferably without causing any interference, thereby avoiding the possibility of the needle 5 coming out of the hollow body 20.

FIGS. 9 and 10 show a further variant of the invention, the only difference with the embodiment of FIGS. 7-8 being that the ring 45 has no fins 32 and directly fits around the needle 5, whereas the stopping means 15 at the needle 5 consist of a ridge 46 or thickening nearby the needle point 18. In this way, the side 47 of the ring 45 forms an abutment for the ridge 46.

An advantage of this embodiment consists in the fact that the scraping means 33 and the abutment means cooperating with the ridge 46 are formed by one and the same part, namely said ring 45. Furthermore, this ring 45 also acts as blocking means 19, resulting in that it simultaneously fulfills three functions.

FIGS. 11 and 12 relate to a further embodiment. An important difference with the embodiment of FIGS. 9 and 10 consists in that the tongues 40-41 and the ring 45 are dimensioned such that in the non-operative state A of the protective device 1 there is no contact between the tongues 40-41 and the needle 5 and furthermore also during the entire retraction of the needle 5 no such contact takes place. FIG. 12 shows an intermediate position, which demonstrates that the tongues 40-41 nicely close around the needle point 18, without touching the latter. As explained in respect to the embodiment of FIGS. 1 to 6, this offers the advantage that the tongues 40-41 are not acting as scraping elements, resulting in that no drops of blood or other fluids are collected at these tongues 40-41, thereby avoiding that such drops are catapulted towards the passage opening 24.

In all embodiments the needle hub 6 may be provided of one or more prolongated parts which at least partially surround the actual protective means 14, in other words surround the hollow body or housing 20. Such needle hub 6 is applied in the embodiment of FIGS. 11 and 12 and is shown on itself in FIG. 13. More particularly, this needle hub 6 comprises prolongations 48-49-50, respectively in the lateral and partially in the upper part thereof. This further improvement is intended to prevent the possibility that the operator can disconnect the cannula needle 2 without activating the protective device 1.

Preferably, the needle 5 is made of AISI 304 steel, and the protective means 14 and the cannula 3 of acetal resin or polypropylene or polyethylene.

According to an important preferred aspect of the invention, which is mentioned in the introductory portion of the description, the scraping means comprise a scraping ring which cooperates with the needle 5, said scraping ring for all positions being located inside the housing at a distance from the rear side of the rear wall or end wall of said housing. In the previously described embodiments, this is demonstrated by means of the distance D which is indicated in the FIGS. 5, 8 and 10.

The main advantage of this invention is that it provides a protective device for a cannula needle to avoid the risk of contact with a patient's body fluids or with drugs wetting the needle, and of accidental pricking and wounds, which device is very efficient in many aspects.

The device is small and compact and thus easy to use and very versatile.

Another advantage is that it provides a protective device that is simple to construct and assemble and is therefore economic.

A further advantage is that it supplies a needle guaranteeing maximum protection for the operator during the operation of extracting the needle from the cannula.

The present invention is in no way limited to the forms of embodiment described by way of example and represented in the figures, however such protective device, as well as cannula needle assemblies and needles provided with such protective device can be realized in various forms and dimensions without leaving the scope of the invention.

The invention claimed is:

1. A protective device for a needle, more particularly for a catheter introducing needle, the protective device comprising:
   protective means for preventing re-use of the needle, the protective means being slidably cooperable with the needle,
   the protective means including a safety means for placing at least one part of the safety means in front of the needle point upon retraction of the needle through the protective means and a blocking means for cooperating with the safety means for releasing the safety means from a blocked position into an unblocked position when the protective device passes from a non-operative state into an operative state,
   the safety means and the blocking means being located and operable for the part or parts of the safety means to remain at a distance from the needle when the part or the parts of the safety means are placed in front of the needle point during an entire retraction of the needle,
   the blocking means being shiftable with respect to the safety means wherein a shifting movement of the blocking means causes the safety means to be released from a blocked position into an unblocked position, and
   the blocking means being cooperable with the needle in such a manner that a displacement and retraction of the needle also causes the shifting movement of the blocking means.

2. The protective device according to claim 1 further comprising the blocking means including a sliding ring located around the needle.

3. The protective device according to claim 1 further comprising:
   the part or the parts of the safety means being elastically bendable such that it or they is or are urged into a path of the needle respectively upon retraction of the needle, and
   wherein the part or the parts in a blocked position are kept at least substantially out of the path of the needle by the blocking means.

4. The protective device according to claim 1 further comprising the protective means includes an extension piece for a catheter hub and the extension piece includes a coupling means for releasably coupling the extension piece to the catheter hub.

5. The protective device according to claim 1 further comprising the needle being attached in a needle hub and the needle hub having one or more prolongations which at least partially surround the protective means.

6. The protective device according to claim 1 further comprising
   the protective means including one or more safety tongues which upon retraction of the needle are automatically positioned in front of a needle point of the needle, thereby preventing the needle from being re-used, and wherein the tongues remain at a distance from the needle during an entire retraction movement of the needle.

7. The protective device according to claim 1 further comprising:
   a hollow body including a housing,
   the hollow body being slidably cooperable with the needle for retracting the needle into a position in which a needle point of the needle is located in the hollow body, and
   a scraping ring cooperable with the needle and located inside the housing at a distance from a rear side of a rear wall of the housing.

8. The catheter introducing needle according to claim 1 further comprising:
   the protective device including a hollow body forming a housing,
   the body slidably cooperating with the needle such that the needle can be retracted into a position in which the needle point is located in the hollow body, and
   a scraping ring which cooperates with the needle and is located inside the housing at a distance from the rear side of a rear wall of the housing.

9. The protective device according to claim 1 further comprising the part or the parts of the safety means include a safety tongue or safety tongues, respectively.

10. The protective device according to claim 9 further comprising the safety means including a pair of safety tongues, which, from opposite sides of the needle, can be brought onto a path of the needle.

11. The protective device according to claim 1 further 1 comprising the safety means and the blocking means being housed in a hollow body having passage openings for the needle.

12. The protective device according to claim 11 further comprising
   a scraping means for drying the needle when the protective device passes from the non-operative state to the operative state.

13. The protective device according to claim 12 further comprising the scraping means being formed by and/or fixed at the blocking means.

14. The protective device according to claim 12 further comprising the scraping means comprise a ring or a plastic O-ring around the needle.

15. A protective device for a needle, more particularly for a catheter introducing needle, the protective device comprising:
   protective means for preventing re-use of the needle, the protective means being slidably cooperable with the needle,
   the protective means including a safety means for placing at least one part of the safety means in front of the needle point upon retraction of the needle through the protective means and a blocking means for cooperating with the safety means for releasing the safety means from a blocked position into an unblocked position when the protective device passes from a non-operative state into an operative state,
   the safety means and the blocking means being located and operable for the part or parts of the safety means to remain at a distance from the needle when the part or the parts of the safety means are placed in front of the needle point during an entire retraction of the needle, and
   the protective means and the needle comprising a stopping means acting as abutment means between the protective means and the needle for preventing the needle from leaving the protective means and defining an end position when retracting the needle.

16. The protective device according to claim 15 further comprising the stopping means at the needle includes an annular groove or a ridge or thickening on an outside of the needle and the stopping means at the protective means are formed by the blocking means or by abutment parts cooperating with the blocking means.

17. A protective device for a needle, more particularly for a catheter introducing needle, the protective device comprising:

the protective means for preventing re-use of the needle, the protective means being slidably cooperable with the needle, the protective means including a safety means for placing at least one part of the safety means in front of the needle point upon retraction of the needle through the protective means and a blocking means for cooperating with the safety means for releasing the safety means from a blocked position into an unblocked position when the protective device passes from a non-operative state into an operative state, the safety means and the blocking means being located and operable for the part or parts of the safety means to remain at a distance from the needle when the part or the parts of the safety means are placed in front of the needle point during an entire retraction of the needle, the blocking means being shiftable with respect to the safety means wherein a shifting movement of the blocking means causes the safety means to be released from a blocked position into an unblocked position, the blocking means being cooperable with the needle in such a manner that a displacement and retraction of the needle also causes the shifting movement of the blocking means, a proximal end of the needle being attached in a needle hub, and the needle hub including at least one part which, in a most forward position of the needle, cooperates with the protective means for preventing the blocking cleans from carrying out the shifting movement.

18. A safety cannula needle assembly comprising:

a protective device including a protective means for preventing re-use of the needle, the protective device being slidably cooperable with the needle, the protective means including a safety means having at least one part which, upon retraction of the needle through the protective means, is operable for being placed in front of a needle point of the needle and prevent the reuse of the needle, a blocking means cooperable with the safety means for releasing the safety means from a blocked position into an unblocked position when the protective device passes from a non-operative state into an operative state, the safety means and the blocking means being located and operable for the part of the safety means to remain at a distance from the needle when the part or the parts of the safety means are placed in front of the needle point during an entire retraction of the needle, the blocking means being shiftable with respect to the safety means wherein a shifting movement of the blocking means causes the safety means to be released from a blocked position into an unblocked position, and the blocking means being cooperable with the needle in such a manner that a displacement and retraction of the needle also causes the shifting movement of the blocking means.

19. A catheter introducing needle comprising:

a protective device including a protective means for slidably cooperating with the needle and the protective means including one or more safety tongues wherein upon retraction of the needle are automatically positioned in front of a needle point of the needle for preventing the needle from being re-used and the tongues remain at a distance from the needle when the part or the parts of the safety means are placed in front of the needle point during an entire retraction of the needle, a blocking means for cooperating with the safety means for releasing the safety means from a blocked position into an unblocked position when the protective device passes from a non-operative state into an operative state, the blocking means being shiftable with respect to the safety means wherein a shifting movement of the blocking means causes the safety means to be released front a blocked position into an unblocked position, and the blocking means being cooperable with the needle in such a manner that a displacement and retraction of the needle also causes the shifting movement of the blocking means.

* * * * *